United States Patent [19]

Kimizuka et al.

[11] Patent Number: 5,045,631

[45] Date of Patent: Sep. 3, 1991

[54] POLYPEPTIDES WITH CELL-SPREADING ACTIVITY

[75] Inventors: Fusao Kimizuka, Ohmihachiman; Tatsuru Kinoshita, Kyoto; Yoh'ichi Ohdate, Amagasaki; Yuki Taguchi, Otsu; Ikunoshin Kato, Uji, all of Japan

[73] Assignee: Takara Shuzo Co., Ltd., Kyoto, Japan

[21] Appl. No.: 310,170

[22] Filed: Feb. 13, 1989

[30] Foreign Application Priority Data

Feb. 16, 1988 [JP] Japan .................................. 63-31820

[51] Int. Cl.$^5$ ............................................. C07K 13/00
[52] U.S. Cl. ..................................... 530/350; 530/382
[58] Field of Search ................................ 530/350, 382

[56] References Cited

U.S. PATENT DOCUMENTS 4,517,686  5/1985  Ruoslahti et al. .
4,589,881  5/1986  Pierschbacher et al. .
4,614,517  9/1986  Ruoslahti et al. .

FOREIGN PATENT DOCUMENTS 0207751  6/1986  European Pat. Off. .

OTHER PUBLICATIONS

K. Sekiguchi & S. Hakomori. "Functional Domain Structure of Fibronectin." Proc. Natl. Acad. Sci, U.S.A., 77, 2661–2665, May 1980.

M. D. Pierschbacher, E. G. Hayman & E. Ruoslahti. "Location of the Cell-Attachment Site in Fibronectin with Monoclonal Antibodies and Proteolytic Fragments of the Molecule." Cell, 26, 259–267, Oct. 1981.

M. D. Pierschbacher & E. Ruoslahti. "The Cell Attachment Domain of Fibronectin. Determination of the Primary Structure." J. Biol. Chem., 257, 9593–9597, Aug. 1982.

M. D. Pierschbacher, E. G. Hayman & E. Ruoslahti. "Synthetic Peptide with Cell Attachment Activity of Fibronectin." Proc. Natl. Acad. Sci. U.S.A., 80, 1224–1227, Mar. 1983.

M. D. Pierschbacher & E. Ruoslahti. "Cell Attachment Activity of Fibronectin Can Be Duplicated by Small Synthetic Fragments of the Molecule." Nature, 309, 30–33, May 1984.

A. R. Kornblihtt, K. Vibe-Pedersen & F. E. Baralle. "Human Fibronectin: Cell Specific Alternative mRNA Splicing Generates Polypeptide Chains Differing in the Number of Internal Repeats." Nucl. Acids Res., 12, 5853–5868, Jul. 1984.

M. D. Pierschbacher & E. Ruoslahti. "Variants of the Cell Recognition Site of Fibronectin that Retain Attachment-Promoting Activity." Proc. Natl. Acad. Sci. U.S.A., 81, 5985–5988, Oct. 1984.

A. R. Kornblihtt, K. Umezawa, K. Vibe-Pedersen & F. D. Baralle. "Primary Structure of Human Fibronectin: Differential Splicing May Generate at Least 10 Polypeptides From a Single Gene." EMBO J., 4, 1755–1759, 1985.

S. K. Akiyama, E. Hasegawa, T. Hasegawa & K. M. Yamada. "The Interaction of Filbronectin Fragments with Fibroblastic Cells." J. Biol. Chem., 260, 13256–13260, Oct. 1985.

M. Obara, M. S. Kang, S. Rocher-Dufour, A. Kornblihtt, J. P. Thiery & K. M. Yamada. "Expression of the Cell-binding Domain of Human Fibronectin in *E. coli*." FEBS Lett., 213, 261–264, Mar. 1987.

The Journal of Biological Chemistry, "The Interaction of Fibronectin Fragments with Fibroblastic Cells", vol. 260, No. 24, Issue of Oct. 25, pp. 13256–13260, 1985.

The Journal of Biological Chemistry, "Domain Structure of the Carboxylterminal Half of Human Plasma", vol. 258, No. 5, Issue of Mar. 10, pp. 3332–3340, 1983.

*Primary Examiner*—Margaret Moskowitz
*Assistant Examiner*—Shelly J. Guest
*Attorney, Agent, or Firm*—Armstrong, Nikaido, Marmelstein, Kubovcik & Murray

[57] ABSTRACT

A polypeptide having the cell-spreading activity of human fibronectin. Methods of preparing the polypeptide are described.

2 Claims, No Drawings

POLYPEPTIDES WITH CELL-SPREADING ACTIVITY

This invention relates to a protein which has cell-spreading activity like that of fibronectin. More particularly, the invention relates to a polypeptide which has the cell-spreading activity of fibronectin of human origin; and also to a method for the preparation of said polypeptide.

Fibronectin is a multifunctional glycoprotein which is widely distributed in a variety of animal tissues and body fluids and also on the surface of cultured cells and elsewhere. This compound has various physiological effects, such as causing attachment, spreading, migration, differentiation, proliferation, and phagocytosis by cells, among others. This glycoprotein participates in such activities as tissue reconstruction, tissue construction, and protection from infection.

Fibronectin is a polypeptide with a molecular weight of about 250,000 and is a dimer with an S—S bond in the vicinity of the C-terminus. The amino acid sequence of this molecule contains 3 different types of internal repeats, and can be classified as types I, II and III. In addition, there are domain structures which have various functions, with the effect of cell attachment and spreading and the ability to bind to collagen, heparin, fibrin, etc. Of these domains, industrial applications of the biological activity related to the cell attachment and spreading domain have been considered; for example, in the preparation of a coating agent for a substrate for culture, it is possible to use this function in the preparation of a substrate to which cells will bind. Also, this function can be used as an accelerator of cell binding in such preparations as collyrium, lotions, and agents for the healing of wounds. Cell spreading is a phenomenon that follows after cell attachment. For cells to proliferate, with some exceptions, it is necessary for the phenomenon of spreading to take place, not cell attachment alone.

The basic structure which is the minimum essential structure for the cell-attachment domain of fibronectin is the sequence Arg-Gly-Asp-Ser (Nature, 309 1984, 30–33). Japanese Laid-Open Patent (Tokuhyo) 84-501548 discloses a peptide with cell-attachment activity, that is a polypeptide of the molecular weight of 11,500 and that contains this sequence among its sequence with 108 amino acid residues.

However, the cell-attachment activity of this polypeptide with the molecular weight of 11,500 is much weaker than that of fibronectin of natural origin, and it is not necessarily possible to make use of it in the practical applications mentioned above. This difficulty is discussed, for example, in *J. Biol. Chem.*, 260 (1985), 13256–13260. Also, the inventors of this invention have constructed the polypeptide of the molecular weight of 11,500 mentioned above by means of genetic engineering, and compared its cell-spreading activity to that of fibronectin of natural origin with the use of normal rat kidney (NRK) cells. The results were that, whereas fibronectin gave noticeable activity at the dose of 0.1–1 μg/well, the dose of 50 μg/well of the polypeptide with the molecular weight of 11,500 did not have any such activity.

The object of this invention is to identify the amino acid sequence that has substantial cell-spreading activity as the peptide of the cell-spreading domain of fibronectin and to provide a method for producing the same.

Briefly the present invention relates to polypeptides with cell-spreading activity, which have an amino acid sequence represented by the following general formula [I]:

X—Glu Gln His Glu Ser Thr Pro Leu Arg Gly
Arg Gln Lys Thr Gly Leu Asp Ser Pro Thr
Gly Ile Asp Phe Ser Asp Ile Thr Ala Asn
Ser Phe Thr Val His Trp Ile Ala Pro Arg
Ala Thr Ile Thr Gly Tyr Arg Ile Arg His
His Pro Glu His Phe Ser Gly Arg Pro Arg
Glu Asp Arg Val Pro His Ser Arg Asn Ser
Ile Thr Leu Thr Asn Leu Thr Pro Gly Thr
Glu Tyr Val Val Ser Ile Val Ala Leu Asn
Gly Arg Glu Glu Ser Pro Leu Leu Ile Gly
Gln Gln Ser Thr Val Ser Asp Val Pro Arg
Asp Leu Glu Val Val Ala Ala Thr Pro Thr
Ser Leu Leu Ile Ser Trp Asp Ala Pro Ala
Val Thr Val Arg Tyr Tyr Arg Ile Thr Tyr
Gly Glu Thr Gly Gly Asn Ser Pro Val Gln
Glu Phe Thr Val Pro Gly Ser Lys Ser Thr
Ala Thr Ile Ser Gly Leu Lys Pro Gly Val
Asp Tyr Thr Ile Thr Val Tyr Ala Val Thr
Gly Arg Gly Asp Ser Pro Ala Ser Ser Lys
Pro Ile Ser Ile Asn Tyr Arg Thr Glu Ile
Asp Lys Pro Ser Gln Met—Y     [I]

wherein X is either a sequence having the following formula:

Val Pro Pro Pro Thr Asp Leu Arg Phe Thr
Asn Ile Gly Pro Asp Thr Met Arg Val Thr
Trp Ala Pro Pro Pro Ser Ile Asp Leu Thr
Asn Phe Leu Val Arg Tyr Ser Pro Val Lys
Asn Glu Glu Asp Val Ala Glu Leu Ser Ile
Ser Pro Ser Asp Asn Ala Val Val Leu Thr
Asn Leu Leu Pro Gly Thr Glu Tyr Val Val
Ser Val Ser Ser Val Tyr or a sequence same as above except that certain amino acid(s) or peptide(s) is deleted from the N-terminus, and Y is either cysteine or its deletion.

This invention also relates to recombinant plasmids which contain the DNA which codes for the polypeptides with cell-spreading activity having the structure represented by the above general formula [I], and this invention also relates to transformants which carry these recombinant plasmids. The present invention further relates to a method for the preparation of the polypeptides having the structure of the general formula [I] with cell-spreading activity by the cultivation of these transformants and the collection of the polypeptides from the culture medium.

We have found that the polypeptide for which the above mentioned patent application has been filed as having cell attachment activity and which is a polypeptide of 11.5-kDa (with a sequence of 108 amino acids) of fibronectin of human origin (abbreviated FN below), has almost no cell-spreading activity, but that the peptide with the sequence of 283 amino acids (Ala[1235]-Met[1517]) that extends from the N-terminus of said polypeptide does have about the same level of spreading activity as FN; and have accomplished a method for its preparation by use of the techniques of genetic engineering, for which a Japanese patent application was filed on January 5, 1988, with the title of the invention "Polypeptide with cell-spreading activity" (Japanese Patent Application No. 148/88).

In this specification, the superscript numerals affixed to the symbols for amino acids show the number of the amino acid residue counted from the N-terminus of the amino acids of FN based on the EMBL Data Bank.

We have further proceeded research work and have prepared by the use of the techniques of genetic engineering polypeptides with cell-spreading activity which have different chain lengths because of the deletion of amino acid or peptide from the N-terminus of the peptide having a sequence of 283 amino acid residues. We have measured the cell-spreading activity of these polypeptides, and have made clear the relationship between the chain length of the peptide and the cell-spreading activity. Further, in the course of such research work it has been found that there occurs a remarkable change in the expression of the peptide depending on the amino acid sequence in the region of the N-terminus. As a result thereof it has become possible to identify the sequence of a peptide which can be expressed in large amounts in addition to its high level of cell-spreading activity. This invention is based upon those findings.

The invention will be explained in more detail below.

As a method for the preparation by genetic engineering techniques of polypeptides of various lengths with deletions in the region of the N-terminus of the peptide with a sequence of 283 amino acids, it is convenient to use the plasmid pTF301 (Japanese Patent Application No. 148/88 mentioned above), which codes for the peptide with the 283 amino acid sequence that has already been cloned. Thus, first, an appropriate restriction enzyme is used to cleave one site slightly upstream of the initiation codon of pTF301 that codes for the sequence $Ala^{1235}$-$Met^{1517}$ of FN, and then exonuclease is used, by which means it is possible to remove the 5'-end of the sequence. By changes in the reaction conditions, it is possible to obtain a plasmid from which appropriate portions of the 5'-terminus of the coding region have been deleted. Then an appropriate restriction enzyme is used to cleave a site slightly downstream from the termination codon of the coding region of these plasmids, and the DNA which has been cleaved is separated by gel electrophoresis, by which it is possible to obtain fragments of cDNA from which various portions of the 5'-terminal strand have been removed. By the insertion of these cDNA fragments into an appropriate expression vector, it is possible to express peptides of various lengths wherein portions of the N-terminal region of the sequence of $Ala^{1235}$-$Met^{1517}$ (283 amino acid residues) have been deleted.

As the expression vector, any of the well-known vectors can be used. We have obtained satisfactory results with direct expression by the use of the pUC-type vectors in which the distance between the ribosome-binding site and the initiation codon has been made optimum.

Also, by the joining with a transcription-termination signal downstream from the termination (stop) codon of pUC vectors, it is possible to improve the expression level.

Selection of the recombinants which express the peptide with cell-spreading activity can be done conveniently with immunoscreening. That is, expression vectors to which the cDNA fragments of different lengths have been joined are inserted into cells of *Escherichia coli* by the usual methods, and the transformants obtained are raised on nitrocellulose filters, after which they are lysed, and the protein from the cells is fixed on the filters. After the filters are blocked with bovine serum albumin or the like, a monoclonal antibody which recognizes the domain of cell spreading of FN is caused to act. The monoclonal antibody bound to the filter is detected by labelling with a second antibody. In this way, it is possible to select recombinants that express the peptide with the domain for cell spreading.

Next, the recombinants so selected are cultured under conditions suitable for expression, and expression of the peptide with the domain for cell spreading is induced. For verification that expression is taking place, immunoblotting can be used. Thus, the whole-cell protein of the cultured cells is lysed by heat treatment in a buffer containing SDS, and separation is conducted on SDS-polyacrylamide electrophoresis, and the electrophoretic pattern is transferred to a nitrocellulose or nylon membrane. After a monoclonal antibody specific for the cell-spreading domain of FN is incubated with the membrane, an enzyme-labeled second antibody is applied, and the enzyme activity of the bound antibody gives rise to color in a chromogenic material, thereby it is possible to confirm that there is a band of the peptide with the cell-spreading domain.

Purification of the peptide with the domain for cell spreading from the recombinants can be done, for example, as follows. The cell pellet is suspended in a buffer, and the soluble fraction and insoluble fraction are separated by ultrasonification. The insoluble fraction is solubilized in a buffer which contains 7 M urea. The soluble fractions are pooled, and put on a Sepharose 4B column bound with the antibody used in immunoblotting; then, affinity purification is carried out. For elution there is used a buffer in the pH region of 2.3. By the collection of the desired fractions by immunoblotting, it is possible to collect the peptide with the domain for cell spreading. When necessary, further purification by FPLC and HPLC can be done.

The peptide with the cell-spreading domain thus obtained may be measured for its cell-spreading activity toward NRK (normal rat kidney) cells. The sample is dissolved in a buffer, and used to coat microtiter plate wells, after which NRK cells are added, and the plate is incubated for a fixed time at 37° C. The spreading of the cells is observed under a microscope, and the minimum dose of sample per well that gives rise to the expression of cell-spreading activity is compared to the dose needed of FN of natural origin. In this way, the strength of the cell-spreading activity can be expressed.

By the series of experiments described above, it has been found that the cell-spreading activity of the cell-spreading domain of FN varies with the length of the peptide chain from the N-terminus. The peptide with a molecular mass of 11.5 kDa with 108 amino acids had no cell-spreading activity. As the length from the N-terminus increased, activity abruptly comes to be expressed. With 138 amino acids, activity was about 1/25th that of FN; with 206 amino acids, activity was about ⅓ that of FN; with 258 amino acids or 279 amino acids, activity was about the same as that of FN. These peptides with cell-spreading activity can be used as they are or else bound with other peptides by use of a crosslinking agent. As a method for the binding with other peptides, there is, for example, the addition of a cysteine residue at the C-terminus of the peptide, and by the use of a bifunctional crosslinking agent such as 3-(2-pyridyldithio)propionic acid-N-hydroxysuccinimide ester, or SPDP, the cysteine residue can be bound to an amino acid residue of another peptide. It is easy to add a cysteine residue to the C-terminus of a peptide by means of genetic engineering. For example, when the gene that codes for the desired peptide is cloned, the addition of the codon that corresponds to cysteine can be added immediately before the termination codon on the 3'-end (Japanese Patent Application No. 148/88 mentioned above).

The peptide of this invention is desirable to be suited for high level of expression in addition to its strong cell-spreading activity. In this aspect, we have compared the level of expression of various peptides by use of their patterns on SDS-PAGE, and found that the level of expression changes greatly depending on differences in the amino acid sequence in the region of the N-terminus of the peptide. As a result thereof it has been possible to select peptides which have the sequence shown above in the general formula [I].

Among the polypeptides having amino acid sequences represented by the general formula [I], most preferable is the one having the following amino acid sequence (279 amino acids):

Pro Thr Asp Leu Arg Phe Thr Asn Ile Gly
Pro Asp Thr Met Arg Val Thr Trp Ala Pro
Pro Pro Ser Ile Asp Leu Thr Asn Phe Leu
Val Arg Tyr Ser Pro Val Lys Asn Glu Glu
Asp Val Ala Glu Leu Ser Ile Ser Pro Ser
Asp Asn Ala Val Val Leu Thr Asn Leu Leu
Pro Gly Thr Glu Tyr Val Val Ser Val Ser
Ser Val Tyr Glu Gln His Glu Ser Thr Pro
Leu Arg Gly Arg Gln Lys Thr Gly Leu Asp
Ser Pro Thr Gly Ile Asp Phe Ser Asp Ile
Thr Ala Asn Ser Phe Thr Val His Trp Ile
Ala Pro Arg Ala Thr Ile Thr Gly Tyr Arg
Ile Arg His His Pro Glu His Phe Ser Gly
Arg Pro Arg Glu Asp Arg Val Pro His Ser
Arg Asn Ser Ile Thr Leu Thr Asn Leu Thr
Pro Gly Thr Glu Tyr Val Val Ser Ile Val
Ala Leu Asn Gly Arg Glu Glu Ser Pro Leu
Leu Ile Gly Gln Gln Ser Thr Val Ser Asp
Val Pro Arg Asp Leu Glu Val Val Ala Ala
Thr Pro Thr Ser Leu Leu Ile Ser Trp Asp
Ala Pro Ala Val Thr Val Arg Tyr Tyr Arg
Ile Thr Tyr Gly Glu Thr Gly Gly Asn Ser
Pro Val Gln Glu Phe Thr Val Pro Gly Ser
Lys Ser Thr Ala Thr Ile Ser Gly Leu Lys
Pro Gly Val Asp Tyr Thr Ile Thr Val Tyr
Ala Val Thr Gly Arg Gly Asp Ser Pro Ala
Ser Ser Lys Pro Ile Ser Ile Asn Tyr Arg
Thr Glu Ile Asp Lys Pro Ser Gln Met

The invention will be explained in more detail by reference to the following examples. However, this invention is not to be taken to be limited to these examples.

EXAMPLE 1

(1) Preparation of DNA fragments

First, 100 μg of the plasmid pTF301 which codes for peptide 283AA with cell-spreading activity was mixed with a buffer for use with the restriction enzyme XbaI and with 120 units of XbaI in a total volume of 300 μl, and incubated at 37° C. for 2 hours. Then, the DNA was collected by ethanol precipitation. Half of the amount obtained was put into 375 μl of a reaction mixture of buffer for use with BAL 31 nuclease which contained 36 units of BAL 31 nuclease-S, and the mixture was incubated at 30° C.; at 2 minutes of incubation to 8 minutes, 28 μl of the reaction mixture was sampled every 30 seconds, and each sample was added to 20 μl of 0.5M EDTA to stop the reaction. The samples were pooled, and DNA was obtained by phenol treatment and then ethanol precipitation. The DNA obtained was put into 200 μl of a reaction mixture of 7 mM Tris-HCl, pH 7.5, which contained 0.1 mM EDTA, 10 mM NaCl, 7 mM MgCl$_2$, 0.1 mM dATP, dGTP, dCTP, and dTTP, and 2 units of Klenow fragment. The mixture was incubated for 20 minutes at 37° C. The reaction was stopped by treatment at 65° C for 10 minutes, and the reaction mixture was adjusted to the composition of buffer for use with HindIII. Then, to 250 μl of this reaction mixture, 60 units for HindIII was added, and the mixture was incubated for 1 hour at 37° C. This mixture was separated by agarose gel electrophoresis, and the fragments that correspond to the size of 0.5-0.8 kb were cut out; 1 μg was obtained.

(2) Cloning into pUC119N

First, 0.65 μg of the DNA fragments obtained in section (1) above was put into 30 μl of a ligase buffer which contained 0.5 μg of phosphorylated NcoI linker (d[pAGCCATGGCT]), 2.8 units of T4 DNA ligase, 0.5 mM ATP, and 10 mM DTT; and the mixture was incubated overnight at 10° C. After the reaction was stopped by being heated at 65° C for 10 minutes, 24 units of NcoI and 12 units of HindIII were added to this reaction mixture and the mixture was incubated in a total volume of 50 μl for 1 hour at 37° C. This was put on a 1-ml column of Sepharose CL-4B; the free linker was eluted with STE buffer (100 mM NaCl, 10 mM Tris-HCl, and 1 mM EDTA, pH 8.0). Then 300 μl of DNA fraction was obtained and concentrated to 55 μl. Of this, 5.5 μl was added to 1 μl of a solution that contained 0.2 μg of the plasmid pUC119 that had been dephosphorylated by treatment with NcoI and HindIII. To this, 65 μl of solution A and 6.5 μl of solution B from a DNA ligation kit (Takara Shuzo Co., Ltd.) were added, and the mixture was incubated overnight at 16° C. Then 20 μl of the reaction mixture was used to transform cells of *Escherichia coli* HB 101.

In addition, pUC119N was obtained by creation of a NcoI site surrounding the translation initiation codon of the commercially available vector pUC119 (Takara Shuzo Co., Ltd.); the distance between the ribosome-binding site and initiation codon was also changed from 7 to 8 bases. (3) Screening of the expression plasmids.

The transformants obtained in section (2) above were transferred to a nitrocellulose filter (BA85; S & S) on L-agar medium containing 50 μg/ml ampicillin, and cultured overnight at 37° C. The colonies that grew were brought into chloroform vapor for 15 minutes, and the nitrocellulose filter was put into a solution of 50 mM Tris-HCl, pH 7.5, containing 150 mM NaCl, 5 mM MgCl$_2$, 3% bovine serum albumin, 1 μg/ml DNase, and 40 μg/ml lysozyme; the mixture was incubated overnight at room temperature. The filter was treated with an anti-FN monoclonal antibody, FN-10 (Tarara Shuzo Co., Ltd.) which specifically recognizes the cell-spreading domain of FN, and a second antibody labelled with peroxidase was applied, and the hydrogen peroxide gave rise to color in the presence of 4-chloro-1-naphthol, by which the transformants which had appeared were found. By this first screening, 52 clones were selected from 1,300 clones, and each was cultured overnight with agitation at 37° C on 5 ml of L-broth containing 50 μg/ml ampicillin. The whole-cell protein of the cells obtained was separated on SDS-polyacrylamide gel electrophoresis (SDS-PAGE), and immunoblotting was applied, in which the anti-FN monoclonal antibody FN-10 was allowed to react. It was found that polypeptides of the molecular masses of 22 kDa-32 kDa had been produced. For 11 clones, the base sequence of the 5'-end of the inserted fragments was identified; they were found to code amino acid sequences which were respectively 279, 258, 219, 213, 207, 206, 198, 195, 190, 186, and 178 long counting from Met$^{1517}$ as the C-terminus.

The amount of these peptides which were expressed were compared on SDS-PAGE; the peptide which was expressed in the greatest amount was a peptide with a sequence 279 amino acids long (accounting for about 20% of the total whole-cell protein); next were peptides with sequence 206 and 258 amino acids long.

The plasmid which expressed the peptide with the sequence 279 amino acids long was designated pTFD707, and the plasmid which expressed the peptide with the sequence 258 amino acids long was designated pTFD202. At the N-terminus of the peptides expressed by pTFD707 and pTFD202, there was a sequence (GCT) attached that corresponding to alanine of vector origin. This sequence was removed by site-specific mutogenesis (see Japanese Patent Application No. 148/88 mentioned above). Also, in order to raise the level of expression, the HindIII-SalI fragment with a 1 pp terminator sequence was removed from the secretion-expression vector pIN-III-ompA-I, and joined with the HindIII-SalI site of pTFD707 and pTFD202, by which means plasmide designated pTF7021 and pTF2021 were obtained.

Escherichia coli JM109 carrying pTF7021 was designated Escherichia coli JM 109/pTF7021, and Escherichia coli JM109 carrying pTF2021 was designated Escherichia coli JM109/pTF2021; the original forms were deposited on Feb. 3, 1988 at the Fermentation Research Institute of the Agency for Science and Technology, 1-3, Higashi 1 chome Tsukuba-shi Ibaraki-ken 305, Japan, as follows: the original form of pTF2021 as FERM BP-1940 and the original form of pTF7021 as FERM BP-1941.

When JM109/pTF7021 cells were cultured and the expressed polypeptide with cell-spreading activity was investigated, it was found that this peptide accounted for at least 30% of the peptides expressed in terms of whole-cell protein.

(4) Cloning and expression of the DNA fragment that code for the Asn$^{1380}$-Met$^{1517}$ sequence of 138 amino acids of FN.

First, a 1.3-kb fragment of pTF301 was obtained by restriction degradation of EcoRI and SalI, and purified on gel electrophoresis. Separately, a 2.15-kb fragment of pUC18 was obtained by restriction degradation by EcoRI and SalI and purified in the same way. The two kinds of fragments were joined by the use of T4 DNA ligase, and used to transform Escherichia coli HB101. The transformants obtained were cultured and their expression was checked by the use of immunoblotting.

EXAMPLE 2

Purification of the peptide with the cell-spreading domain

Plasmid pTF7021 obtained by the joining of an expression vector and the DNA that codes for the Pro$^{123}$-9Met$^{1517}$ sequence of FN (a sequence of 279 amino acid residues) was introduced into Escherichia coli JM109, giving Escherichia coli JM109/pTF7021, and these cells were cultured overnight with shaking at 37° C in 5 ml of L-broth containing 50 μg/ml ampicillin in a test tube. This was used to inoculate a 2-1 Erlenmeyer flask containing 500 ml of the same medium, and culture was continued at the agitation rate of 180 r.p.m. When absorbance at 660 nm had reached 0.3, 2 mM IPTC (isopropyl-β-thiogalactoside) was added, and the cells were harvested 20 hours later. One portion of the cells obtained was used in immunoblotting. The whole-cell protein was isolated by SDS-PAGE, and the electrophoretic pattern was transferred to a nitrocellulose membrane. Then a monoclonal antibody (FN-10, Takara Shuzo Co., Ltd.) that specifically recognizes the cell-spreading domain of FN was applied, after which a second antibody labelled with peroxidase was applied. The activity of the peroxidase bound to the second antibody gave rise to color in the presence of 4-chloronaphtol and hydrogen peroxide, and it was found that the desired band in the region of 35 kDa was present. Next, the whole-cell pellet was suspended in a solution of 10 mM Tris-HCl, pH 7.5, containing 5 mM EDTA and 5 mM mercaptoethanol, and ultrasonification was conducted. This suspension was centrifuged and the supernatant was obtained and dialyzed against 20 mM Tris-HCl (pH 7.5). The inner dialysis liquid was put on a Sepharose 4B column (8 ml) bound with the monoclonal antibody FN-10. The column was washed with washing buffer A (20 mM Tris-HCl, pH 8.0, and 0.15 M KCl), and then with washing buffer B (20 mM Tris-HCl, pH 6.4, and 0.15 M KCl). Finally, the eluting buffer (50 mM glycine-HCl, pH 2.3, and 0.2 M KCl) was used, and fractions were obtained. The desired fractions were obtained by immunoblotting, desalted, and lyophilized, and about 5 mg of almost pure peptide was obtained by electrophoresis. Next, said peptide was treated with aminopeptidase P (Enzyme Handbook, p. 534 (1983), Asakura Publishers), and the N-terminal methionine was removed, after which the peptide was purified again by the same method as described above. The 10 or so amino acids residues in the amino acids residues in the amino acid sequence starting from the N-terminus were studied, and it was found that the sequence was Pro-Thr-Asp-Leu-Arg-Phe-Thr-Asn-Ile-Gly, which agreed with the N-terminal sequence of the desired peptide.

The recombinants which correspond respectively to the peptides with sequences 258, 219, 206, 178, and 138 amino acids long were also cultured by the same method and purified; each of the peptides were isolated, and the structure of the N-terminal region was identified.

EXAMPLE 3

Measurement of Cell-spreading Activity

The cell-spreading activity of all of the polypeptides obtained in Example 2 and of FN and the peptides with 283 and 108 amino acids was measured by the method of Ruoslahti et al. (Methods in Enzymology, 82, 803-831, 1981). The samples was diluted stepwise in physiological saline and distilled water, and 50 μl of the resultant solution was injected into the wells of a 96-well microtitre plate, which was then incubated overnight at 4° C in order to allow the sample to adhere to the wells. Then, phosphate-buffered saline (PBS) was used to wash the plate twice, 100 μl of 3% BSA was added to each well, and the plate was incubated for one hour at 37° C. The plate was washed twice with PBS, and then normal rat kidney (NRK-49F) cells suspended to the concentration of 10$^6$ cells/ml in Eagle's Minimum Essential Medium (MEM) were added in the amount of 100 μl/well, and the plate was incubated for 2-3 hours at 37° C. The NRK-49F cells that were used were obtained as a lyophilized strain for storage, and first preincubated and then treated with trypsin before use. The spreading of the cells was observed under a microscope, and the minimum dose needed to have cell-spreading activity was calculated. These results are shown in Table 1.

Table 1 also shows the amount of peptide expressed by the transformant recombinants, relative to the amount of the peptide with the sequence of 283 amino acids given as +.

TABLE 1

| Polypeptide (length of amino acid sequence) | Minimum dose for cell spreading μg/well (p mole/well) | Relative amount expressed |
| --- | --- | --- |
| Ile$^{1410}$—Met$^{1517}$ (108) | >50 (>4400) | |
| Asn$^{1380}$—Met$^{1517}$ (138) | 0.31 (19.7) | |
| Ala$^{1340}$—Met$^{1517}$ (178) | 0.08 (4.0) | |
| Glu$^{1312}$—Met$^{1517}$ (206) | 0.05 (2.2) | +++ |
| Pro$^{1299}$—Met$^{1517}$ (219) | 0.04 (1.8) | ++ |
| Pro$^{1260}$—Met$^{1517}$ (258) | 0.03 (1.2) | +++ |
| Pro$^{1239}$—Met$^{1517}$ (279) | 0.03 (1.0) | ++++ |
| Ala$^{1235}$—Met$^{1517}$ (283) | 0.03 (1.0) | + |
| FN (2324) | 0.18 (0.8) | |

As explained above in detail, this invention provides a peptide which has cell-spreading activity essentially the same as that of FN, and also provides a method for its preparation by the use of genetic engineering. The polypeptides mentioned above can be used as a pharmaneutical preparation for such uses as for the healing of wounds, in collyria, for the prevention of metastases from cancer, for the implantation of artificial organs into the body, and the like. It can also be used in cosmetics, toothpaste, and the like.

What we claim is:

1. A polypeptide with cell-spreading activity which consists of the following amino acid sequence beginning with the amino terminus:

Pro Thr Asp Leu Arg Phe Thr Asn Ile Gly
Pro Asp Thr Met Arg Val Thr Trp Ala Pro
Pro Pro Ser Ile Asp Leu Thr Asn Phe Leu
Val Arg Tyr Ser Pro Val Lys Asn Glu Glu
Asp Val Ala Glu Leu Ser Ile Ser Pro Ser
Asp Asn Ala Val Val Leu Thr Asn Leu Leu
Pro Gly Thr Glu Tyr Val Val Ser Val Ser
Ser Val Tyr Glu Gln His Glu Ser Thr Pro
Leu Arg Gly Arg Gln Lys Thr Gly Leu Asp
Ser Pro Thr Gly Ile Asp Phe Ser Asp Ile
Thr Ala Asn Ser Phe Thr Val His Trp Ile
Ala Pro Arg Ala Thr Ile Thr Gly Tyr Arg
Ile Arg His His Pro Glu His Phe Ser Gly
Arg Pro Arg Glu Asp Arg Val Pro His Ser
Arg Asn Ser Ile Thr Leu Thr Asn Leu Thr
Pro Gly Thr Glu Tyr Val Val Ser Ile Val
Ala Leu Asn Gly Arg Glu Glu Ser Pro Leu
Leu Ile Gly Gln Gln Ser Thr Val Ser Asp
Val Pro Arg Asp Leu Glu Val Val Ala Ala
Thr Pro Thr Ser Leu Leu Ile Ser Trp Asp
Ala Pro Ala Val Thr Val Arg Tyr Tyr Arg
Ile Thr Tyr Gly Glu Thr Gly Gly Asn Ser
Pro Val Gln Glu Phe Thr Val Pro Gly Ser
Lys Ser Thr Ala Thr Ile Ser Gly Leu Lys
Pro Gly Val Asp Tyr Thr Ile Thr Val Tyr
Ala Val Thr Gly Arg Gly Asp Ser Pro Ala
Ser Ser Lys Pro Ile Ser Ile Asn Tyr Arg
Thr Glu Ile Asp Lys Pro Ser Gln Met.

2. A polypeptide with cell-spreading activity which consists of the following amino acid sequence beginning with the amino terminus:

Pro Ser Ile Asp Leu Thr Asn Phe Leu
Val Arg Tyr Ser Pro Val Lys Asn Glu Glu
Asp Val Ala Glu Leu Ser Ile Ser Pro Ser
Asp Asn Ala Val Val Leu Thr Asn Leu Leu
Pro Gly Thr Glu Tyr Val Val Ser Val Ser
Ser Val Tyr Glu Gln His Glu Ser Thr Pro
Leu Arg Gly Arg Gln Lys Thr Gly Leu Asp
Ser Pro Thr Gly Ile Asp Phe Ser Asp Ile
Thr Ala Asn Ser Phe Thr Val His Trp Ile
Ala Pro Arg Ala Thr Ile Thr Gly Tyr Arg
Ile Arg His His Pro Glu His Phe Ser Gly
Arg Pro Arg Glu Asp Arg Val Pro His Ser
Arg Asn Ser Ile Thr Leu Thr Asn Leu Thr
Pro Gly Thr Glu Tyr Val Val Ser Ile Val
Ala Leu Asn Gly Arg Glu Glu Ser Pro Leu
Leu Ile Gly Gln Gln Ser Thr Val Ser Asp
Val Pro Arg Asp Leu Glu Val Val Ala Ala
Thr Pro Thr Ser Leu Leu Ile Ser Trp Asp
Ile Thr Tyr Gly Glu Thr Gly Gly Asn Ser
Pro Val Gln Glu Phe Thr Val Pro Gly Ser
Lys Ser Thr Ala Thr Ile Ser Gly Leu Lys
Pro Gly Val Asp Tyr Thr Ile Thr Val Tyr
Ala Val Thr Gly Arg Gly Asp Ser Pro Ala
Ser Ser Lys Pro Ile Ser Ile Asn Tyr Arg
Thr Glu Ile Asp Lys Pro Ser Gln Met.

* * * * *

UNITED STATES PATENT AND TRADEMARK OFFICE
CERTIFICATE OF CORRECTION

PATENT NO. : 5,045,631
DATED : September 3, 1991
INVENTOR(S) : Fusao KIMIZUKA et al.

It is certified that error appears in the above-identified patent and that said Letters Patent is hereby corrected as shown below:

In claim 2, Column 10, after line 18 of the amino acid sequence, insert --Ala Pro Ala Val Thr Val Arg Tyr Tyr Arg--

Signed and Sealed this

Fifteenth Day of March, 1994

Attest:

BRUCE LEHMAN

Attesting Officer

Commissioner of Patents and Trademarks